US011781962B2

(12) United States Patent
Wang et al.

(10) Patent No.: US 11,781,962 B2
(45) Date of Patent: Oct. 10, 2023

(54) CHARACTERIZATION METHOD OF CLOSED PORES AND CONNECTIVITY OF COAL MEASURE COMPOSITE RESERVOIRS

(71) Applicant: China University of Mining and Technology, Xuzhou (CN)

(72) Inventors: Yang Wang, Xuzhou (CN); Jie Xiang, Xuzhou (CN); Shangbin Chen, Xuzhou (CN); Tong Zhang, Xuzhou (CN); Qingshun Cao, Xuzhou (CN)

(73) Assignee: China University of Mining and Technology, Xuzhou (CN)

( * ) Notice: Subject to any disclaimer, the term of this patent is extended or adjusted under 35 U.S.C. 154(b) by 0 days.

(21) Appl. No.: 18/124,703

(22) Filed: Mar. 22, 2023

(65) Prior Publication Data

US 2023/0258550 A1    Aug. 17, 2023

Related U.S. Application Data

(63) Continuation of application No. PCT/CN2022/103353, filed on Jul. 1, 2022.

(30) Foreign Application Priority Data

Jul. 30, 2021   (CN) .......................... 202110873856.X

(51) Int. Cl.
    *G01B 13/06*   (2006.01)
    *G01N 15/08*   (2006.01)
    (Continued)

(52) U.S. Cl.
    CPC ........... *G01N 15/088* (2013.01); *G01N 1/286* (2013.01); *G01N 23/201* (2013.01);
    (Continued)

(58) Field of Classification Search
    CPC ........... G01N 23/201; G01N 2223/054; G01N 2223/1016
    See application file for complete search history.

(56) References Cited

U.S. PATENT DOCUMENTS

2003/0094032 A1 *   5/2003   Baklanov ............... G01N 15/08
                                                         73/37.5

FOREIGN PATENT DOCUMENTS

CA          1261978       9/1989
CN          104237103     12/2014
            (Continued)

OTHER PUBLICATIONS

Zhao et al. "Pore structure characterization of shales using synchrotron SAXS and NMR cryoporometry" Marine and Petroleum Geology 102 (2019) 116-125.

(Continued)

*Primary Examiner* — Don K Wong
(74) *Attorney, Agent, or Firm* — Stuart H. Mayer; Kaplan Breyer Schwarz, LLP

(57) ABSTRACT

Disclosed is a characterization method of closed pores and connectivity of coal measure composite reservoirs, including collecting samples of coal seams and shales reservoirs, carrying out low-field NMR experiments and NMR freeze-thaw experiments on plunger samples and crushed samples with different particle sizes to obtain cumulative pore volume distribution and differential pore size distribution of the crushed samples, comparing crushed samples with plunger samples for optimal crushed particle sizes, and preliminarily determining a distribution range of closed pores; carrying out SAXS experiments on crushed samples to obtain size distribution and volume of total pores of 1-100 nanometers; calculating pore volume of total pores and closed pore volume in composite reservoirs by low-field NMR experiments results; carrying out non-steady overburden perme- (Continued)

ability experiments and variable factors on plunger samples of coal seams, shales and tight sandstone to characterize the connectivity under influence of pores development and lithologic combinations.

5 Claims, 5 Drawing Sheets

(51) Int. Cl.
    *G01N 24/08*     (2006.01)
    *G01N 33/24*     (2006.01)
    *G01N 1/28*     (2006.01)
    *G01N 23/223*     (2006.01)
    *G01N 23/201*     (2018.01)

(52) U.S. Cl.
    CPC ......... *G01N 23/223* (2013.01); *G01N 24/081* (2013.01); *G01N 33/24* (2013.01)

(56) References Cited

FOREIGN PATENT DOCUMENTS

| CN | 105974092 | 9/2016 |
|---|---|---|
| CN | 108872045 | 11/2018 |
| CN | 108956422 | 12/2018 |
| CN | 110516016 | 11/2019 |
| CN | 112816392 | 5/2021 |
| CN | 113607621 | 11/2021 |

OTHER PUBLICATIONS

Wang et al. "Reservoir characteristics of coal-shale sedimentary sequence in coal-bearing strata and their implications for the accumulation of unconventional gas" Journal of Geophysics and Engineering, J. Geophys. Eng. 15 (2018) 411-420 (10pp).

Sun, "Synchrontron radiation facility-based quantitative evaluation of pore structure heterogeneity and anisotropy in coal" Petroleum Exploration and Development vol. 46, No. 6 Dec. 2019.

Sun, "Porosity Measurement of Crushed Shales Using NMR" Well logging Technology vol. 41, No. 5, Oct. 2017.

Fu, "Analysis and enlightenment of porosity differences between shale plug samples and crushed samples" Petroleum Geology and Experiment, vol. 42, No. 2, Mar. 2020.

Zhang "Connectivity of pores in shale reservoirs and its implications for the developments of shale gas: a case study of the lower silurian longmaxi formation in the sourther sichuan basin" China Academic Journal Electronic, Dec. 2019.

* cited by examiner

CHARACTERIZATION METHOD OF CLOSED PORES AND CONNECTIVITY OF COAL MEASURE COMPOSITE RESERVOIRS

CROSS-REFERENCE TO RELATED APPLICATIONS

This application is a continuation of PCT/CN2022/103353, filed on Jul. 1, 2022 and claims priority of Chinese Patent Application No. 202110873856.X, filed on Jul. 30, 2021, the entire contents of which are incorporated herein by reference.

TECHNICAL FIELD

The present application generally relates to development and evaluation of unconventional natural gas composite reservoirs in coal measures, and in particular to a characterization method of closed pores and connectivity of coal measure composite reservoirs.

BACKGROUND

Coal measures strata are organic-rich sedimentary rock series deposited in paralic or continental environment and containing not only coal seams or coal lines. Coal measure gas includes coalbed methane mainly in adsorbed state, tight sandstone gas and carbonate gas mainly in free state, and shale gas in mixed state. Due to influence of sedimentary and tectonic environment, source-reservoir-cap assemblages of the coal measure gas are complex, with various lithology, interbedded development and remarkable cyclicity. Coal measure reservoirs mainly include the coal seams, shales and the tight sandstone, and methane-based gas mainly occurs in micro-nano scale pores. The pores include interconnected pores and closed pores, which may affect occurrence and migration of the coal measure gas.

At present, evaluation and characterization of the closed pores and connectivity are mainly through following two methods. One method is to crush plunger samples into crushed samples with different particle sizes step by step to measure porosity, and then calculate a proportion of the closed pores; the other is to obtain development situation of the closed pores in a pore size range of about 1-500 nanometer (nm) by mercury penetration, low-temperature liquid nitrogen adsorption, carbon dioxide ($CO_2$) adsorption combined with a small-angle scattering technology. However, the former can't reveal the closed pores in the crushed samples, while the latter has a limited characterization range of the closed pores.

SUMMARY

An objective of the present application is to provide a characterization method of closed pores and connectivity of coal measure composite reservoirs, which combines low-field NMR experiments for measuring porosities of the plunger samples and the crushed samples with SAXS experiments to reveal development of closed pores in coal seams, shales and tight sandstone in the coal measure composite reservoirs in a full scale, and uses non-steady overburden permeability experiments and variable factor under simulated stratum conditions to characterize the connectivity of the coal measure composite reservoirs.

To achieve the above objective, the present application provides a characterization method of closed pores and connectivity of coal measure composite reservoirs, including:

S1, making coal seams and shales in the coal measure composite reservoirs into plunger samples, and carrying out nuclear magnetic resonance (NMR) experiments on the plunger samples to obtain porosities, cumulative pore volume distribution and differential pore size distribution of the plunger samples;

S2, crushing the plunger samples of the coal seams and the shales into crushed samples with different particle sizes respectively, and carrying out NMR freeze-thaw experiments on the crushed samples to obtain cumulative pore volume distribution and differential pore size distribution of the different particle sizes;

S3, determining an optimal crushed particle size for opening the closed pores in the coal seams and the shales based on the cumulative pore volume distribution and the differential pore size distribution of the plunger samples and the different particle sizes, comparing the crushed samples with the plunger samples, calculating closed pore volume opened in a process of the crushing the plunger samples into the crushed samples;

S4, carrying out small-angle X-ray scattering (SAXS) experiments on the crushed samples with the optimal crushed particle size of the coal seams and the shales respectively to obtain pore size distribution and pore volume of total pores (the interconnected pores+the closed pores) in pore size ranges;

S5, determining the pore volume of the total pores and closed pore volume in the coal seams and the shales based on results of the NMR experiments of the plunger samples, the NMR freeze-thaw experiments as well as the SAXS experiments of the crushed samples; and S6, making the plunger samples of the coal seams, the shales and tight sandstone with a same diameter but different heights according to actual drilling reservoir combinations, and carrying out the non-steady overburden permeability experiments to quantitatively characterize the connectivity of the coal measure composite reservoirs under influence of stratum pressure conditions and lithologic combinations.

Optionally, the S1 comprises:

S11, dividing the coal measure composite reservoirs according to the source-reservoir-cap assemblages by a gas and water distribution relationship in a gas-bearing system of the coal measures to obtain the coal seams, the shales and the tight sandstone;

S12, collecting fresh borehole samples from the coal seams and the shales to make multiple groups plunger samples; and S13, carrying out the NMR experiments on the plunger samples, then measuring transverse relaxation time, and calculating the porosities, the cumulative pore volume distribution and the differential pore size distribution of the plunger samples.

Optionally, in the S13, before measuring the transverse relaxation time, the plunger samples used in the NMR experiments are vacuumized, pressurized with 15 megapascal (MPa) and treated with saturated saline for 48 hours (h).

Optionally, the S2 includes: drying the plunger samples after the NMR experiments for 24 h, crushing by a crusher, sieving into the crushed samples with the different particle sizes by a standard mesh screen, then carrying out the NMR freeze-thaw experiments on the crushed samples with the different particle sizes, and calculating by a simplified Gibbs-Thomson thermodynamic equation to obtain the cumulative pore volume distribution and the differential pore size distribution of the different particle sizes.

Optionally, in the NMR freeze-thaw experiments, distilled water is used as a probe solution, its temperature gradually increases from −33 degree Celsius (° C.) to 0° C., and the temperature keeps at each temperature point (integer) for 5 minutes (min).

Optionally, the S4 includes:

S41, carrying out the SAXS experiments on the crushed samples with the optimal crushed particle size of the coal seams and the shales to obtain two-dimensional scattering images, then converting the two-dimensional scattering images into scattering data by a FIT2D software, and converting relative scattering intensity data of standard samples in same experimental environment into absolute scattering intensity of the crushed samples with the optimal crushed particle size;

S42, measuring contents of major elements in the crushed samples with the optimal crushed particle size by an X-ray fluorescence spectrometer, and measuring density data of the standard samples in the same experimental environment, and calculating total porosities, pore volume and pore specific surface area of the crushed samples with the optimal crushed particle size; and S43, importing the scattering data by using a McSAS software based on a Monte Carlo regression principle, setting corresponding parameters, and obtaining the pore size distribution and the pore volume of the total pores in a pore size range of 1-100 nm, Optionally, the S6 includes:

S61, dividing source-reservoir-cap assemblages according to stratum lithology and gas and water distribution revealed by drilling cores, determining vertical upward distribution of the coal measure reservoirs, and obtaining several typical lithological combination types;

S62, making the plunger samples of the coal seams, the shales and the tight sandstone with the same diameter but the different heights and perpendicular to a bedding direction according to the lithological combination types; and S63, carrying out the non-steady overburden permeability experiments method to quantitatively characterize the connectivity of the coal measure composite reservoirs under the influence of the stratum pressure conditions and the lithological combinations, and evaluating the reservoirs combined with closed pores characterization to select the favorable coal measure composite reservoirs.

Compared with the prior art, the application has following advantages.

This application combines the low-field NMR experiments for measuring porosities of the plunger samples and the crushed samples with the SAXS experiments to reveal development of the closed pores in the coal seams, the shales and the tight sandstone in the coal measure composite reservoirs in the full scale. Moreover, the application may not only reveal the unopened closed pores in the crushed samples, greatly improve the range and accuracy of characterization of the closed pores, quantitatively evaluate the closed pores in the coal measure composite reservoirs, but also characterize the connectivity of the coal measure composite reservoirs by combining the non-steady overburden permeability experiments and the variable factor. Existing single lithology permeability experiments may not match the complex coal measure reservoir combinations, while the non-steady overburden permeability experiments and the variable factor may systematically reveal the complex lithology and permeability characteristics of the coal measure reservoir combinations. Therefore, according to the application, the non-steady overburden permeability experiments and the variable factor combined with closed pores evaluation constitutes the characterization method of the closed pores and the connectivity of the coal measure composite reservoirs.

BRIEF DESCRIPTION OF THE DRAWINGS

In order to more clearly explain the embodiments of the present application or the technical solutions in the prior art, the following will briefly introduce the drawings to be used in the embodiments. Obviously, the drawings in the following description are only some embodiments of the present application. For those of ordinary skill in the art, other drawings may be obtained according to these drawings without any creative effort.

FIG. 2(a)-FIG. 2(b) shows a schematic diagram of pore volume distribution and pore size ranges of closed pores obtained by low-field NMR experiments in an embodiment of the application, in which FIG. 2(a) shows a schematic diagram of the pore volume distribution obtained by the low-field NMR experiments and FIG. 2(b) shows a schematic diagram of the pore size ranges of the closed pores obtained by the low-field NMR experiments.

DETAILED DESCRIPTION

The technical schemes of the present application are clearly and completely described below with reference to the drawings, and it is clear that the described embodiments are a part of the embodiments of the present application, and not all of them. Based on the embodiments in the present application, all other embodiments obtained by a person of ordinary skill in the art without making creative labor fall within the scope of protection of the present application.

In order to make the above objective, features and advantages of the application obvious and understandable, the application is further explained in detail below with reference to the drawings and detailed description.

Figure 1:
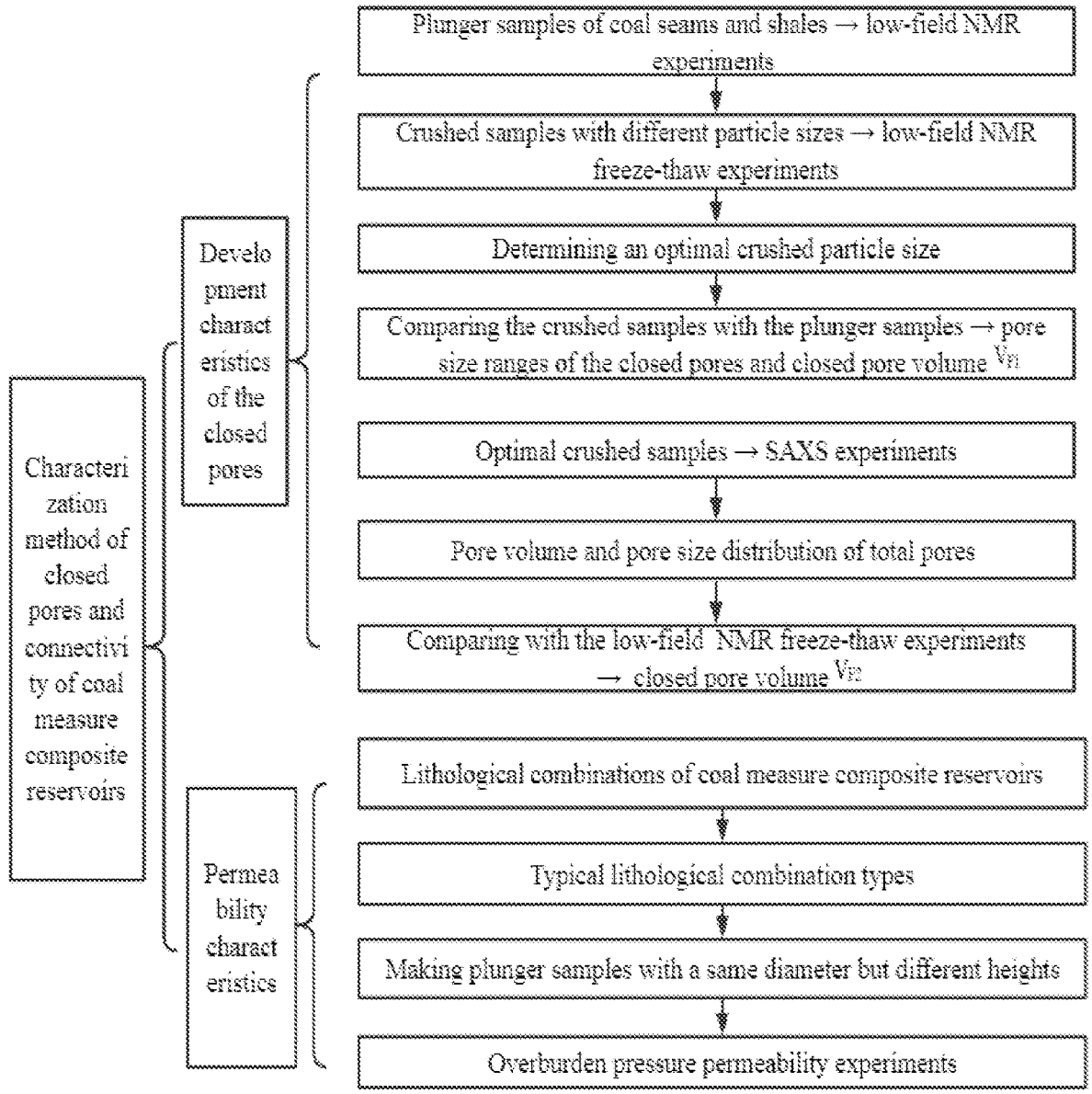
FIG. 1 shows a flow chart of a characterization method of closed pores and connectivity of coal measure composite reservoirs in an embodiment of the application.

As shown in FIG. 1, the application provides a characterization method of closed pores and connectivity of coal measure composite reservoirs, including characterization of the closed pores and characterization of the connectivity. The characterization of the closed pores is carried out by low-field NMR experiments, low-field NMR freeze-thaw experiments and SAXS experiments, so as to reveal the closed pores of coal seams and shales in the coal measure composite reservoirs with low-porosities and low-permeability in full scale, including closed pores opened during crushing plunger samples into crushed samples and closed pores in the crushed samples. Permeability directly indicates the connectivity of the coal measure composite reservoirs. According to vertical distribution of the coal measure composite reservoirs, typical lithologic combination types are determined, plunger samples of different combinations of the coal seams, the shales and tight sandstone are made, and non-steady overburden permeability experiments are carried out.

Figure 2A:
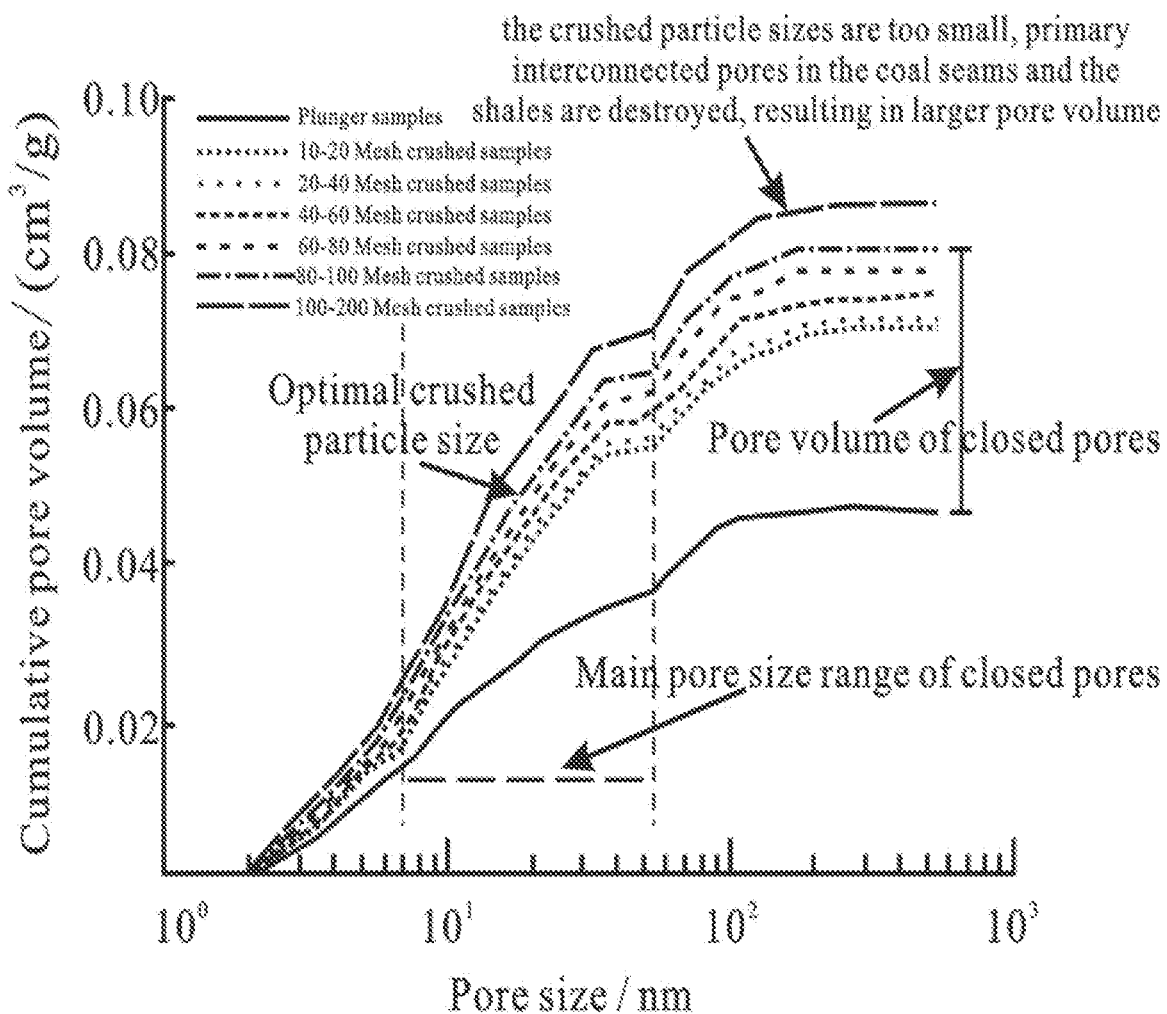
Figure 2B:
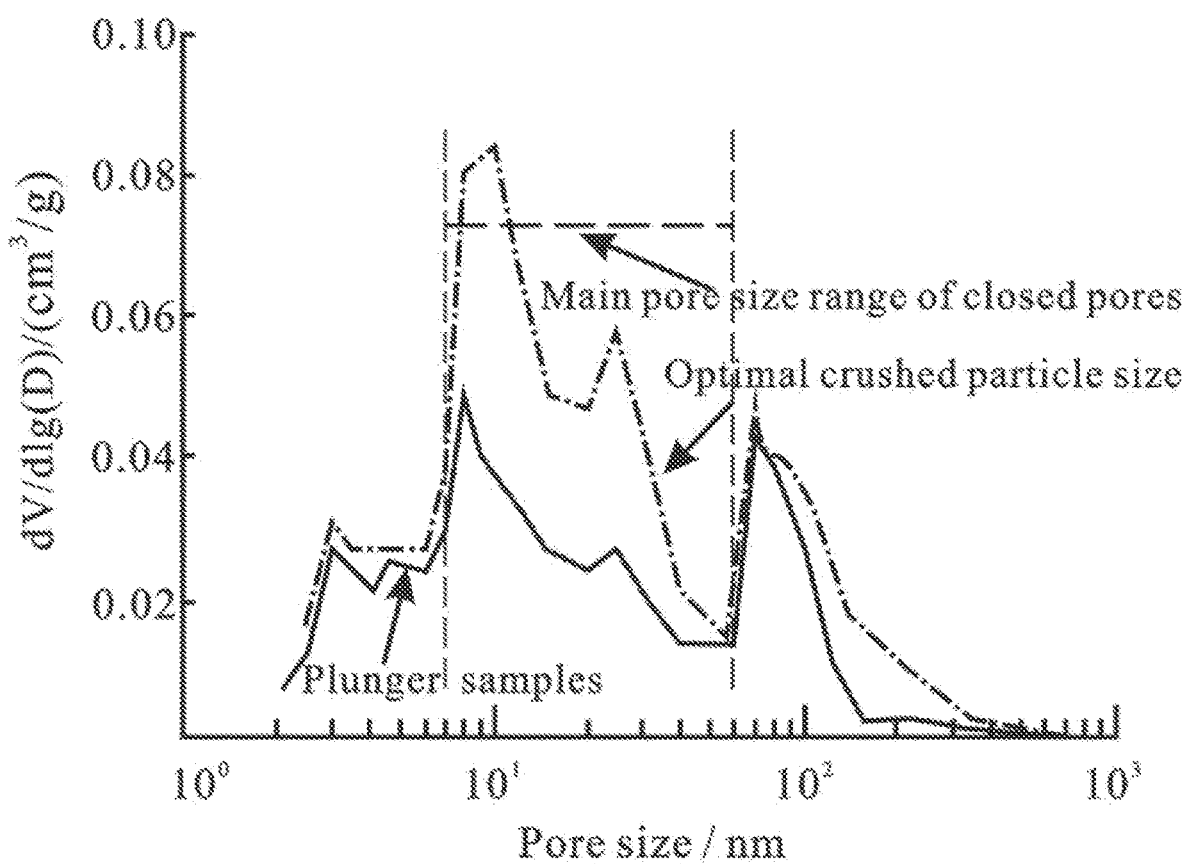
Figure 3:
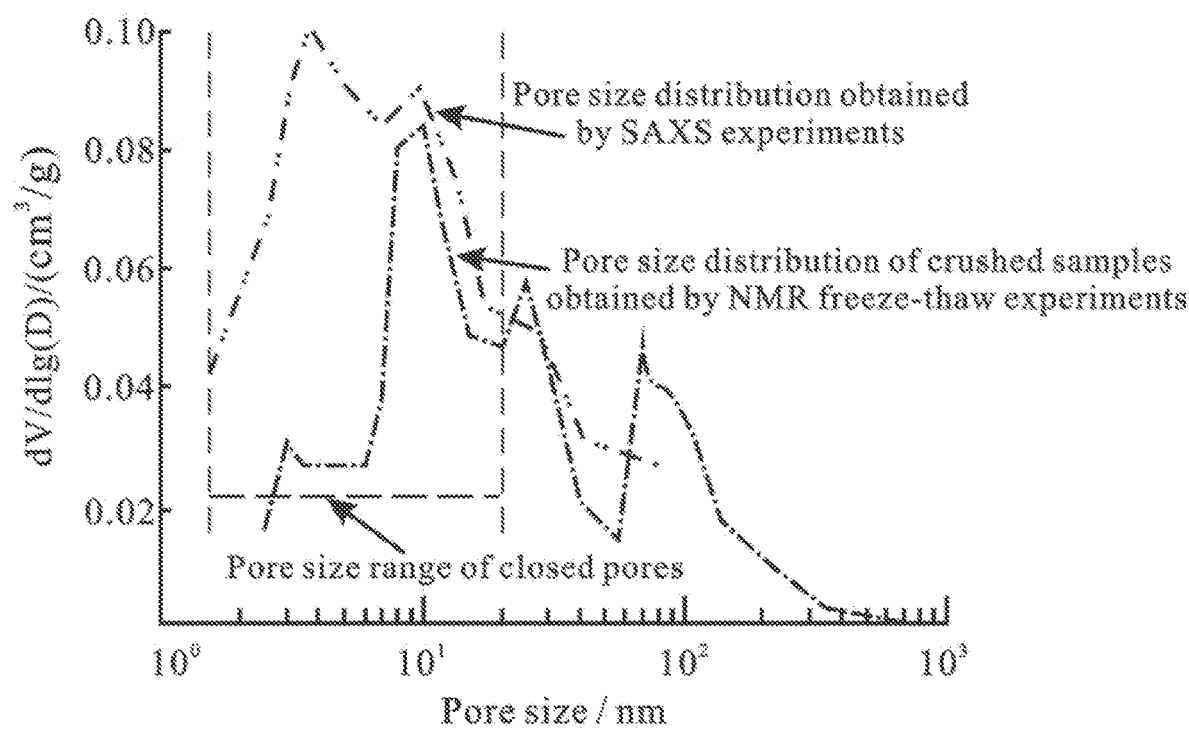
FIG. 3 shows a comparison diagram of pore size distribution of crushed samples with an optimal crushed particle size obtained by SAXS experiments and low-field NMR experiments in an embodiment of the application.
Figure 4:
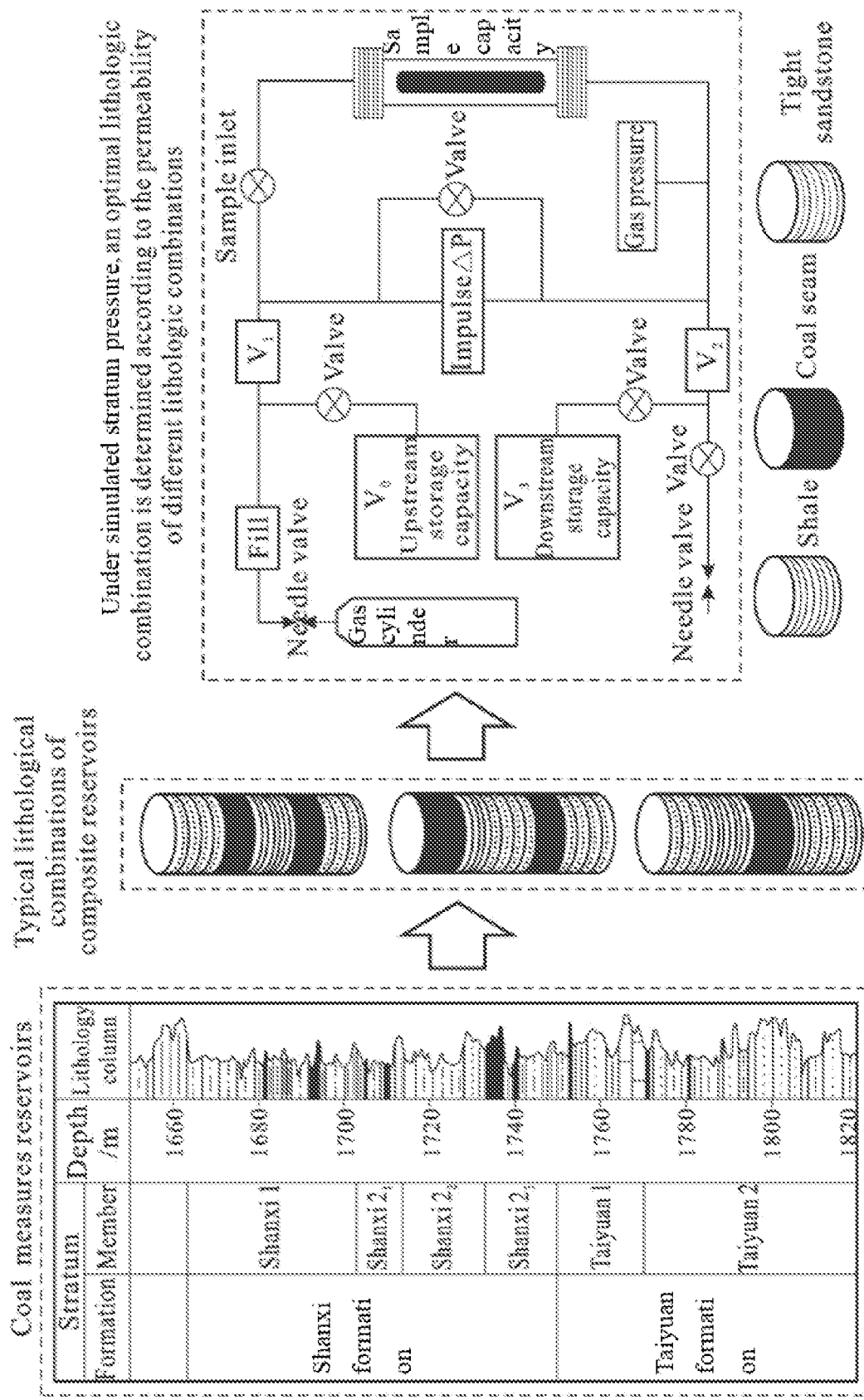
FIG. 4 shows a schematic diagram of several groups of samples of composite reservoirs permeability experiments in an embodiment of the application.

The characterization method of the closed pores and the connectivity of the coal measure composite reservoirs includes:

S1, making the coal seams and the shales in the coal measure composite reservoirs into the plunger samples, and carrying out the low-field NMR experiments on the plunger samples to obtain porosities and pore size distribution of the plunger samples, where the S1 includes:

S11, dividing source-reservoir-cap assemblages according to gas and water distribution in a "Three Gases" gas-bearing system of coal measures, and collecting fresh borehole samples from the coal seams and the shales by wire-electrode cutting perpendicular to a bedding direction for preventing breakage to obtain multiple groups of plunger samples of 10 millimeter (mm)×20 mm; and S12, carrying out the low-field NMR experiments on the plunger samples of the coal seams and the shales, vacuumizing and pressurizing the plunger samples, saturating the plunger samples with brine for 48 h under the pressure of 15 MPa, then measuring the NMR transverse relaxation time ($T_2$) spectrums to reveal total pore characteristics of cores, and calculating total porosities and the pore size distribution of the plunger samples by a formula (1) and a formula (2), where the $T_2$ is expressed as:

$$\frac{1}{T_2} = \rho_2 \frac{S}{V} = \rho_2 \frac{F_s}{r_c}, \text{ and} \quad (1)$$

$$r_c = \rho_2 F_s T_2 = C_2 T_2, \quad (2)$$

where $T_2$ represents the NMR transverse relaxation time, millisecond (ms); $P_2$ represents a transverse relaxation time rate, nanometer per millisecond (nm/ms); S represents a pore surface area, square nanometer ($nm^2$); V represents pore volume, cubic nanometer ($nm^3$); $F_S$ represents pore geometry factor; $r_c$ represents a pore radius, nm; and $C_2$ represents conversion coefficient;

S2, crushing the plunger samples of the coal seams and the shales into crushed samples with different particle sizes respectively, and carrying out the low-field NMR freeze-thaw experiments on the crushed samples to obtain cumulative pore volume distribution and differential pore size distribution of the crushed samples with the different particle sizes, as experimental samples may be reused in the low-field NMR experiments, the plunger samples after the low-field NMR experiments are dried for 24 h to remove residual brine, are crushed by a crusher, then are screened into 10-20 mesh (a particle size 2.000-0.850 mm), 20-40 mesh (a particle size 0.850-0.425 mm), 40-60 mesh (a particle size 0.425-0.250 mm), 60-80 mesh (a particle size 0.250-0.180 mm), 80-100 mesh (a particle size 0.180-0.150 mm) and 100-200 mesh (a particle size 0.150-0.075 mm) with a standard mesh screen, and are measured by the low-field NMR freeze-thaw experiments, where distilled water is used as a probe solution, its temperature gradually increases from −33° C. to 0° C., the temperature keeps at each temperature point (integer) for 5 min, and the pore size distribution is calculated by a simplified Gibbs-Thomson thermodynamic equation, $$\Delta T_m = \frac{K_{GT}}{x}, \quad (3)$$

where x is a pore diameter, nm; $K_{GT}$ is a melting point depression constant, K·nm; and $\Delta T_m$ is variation of material melting points, K;

S3, determining an optimal crushed particle size for opening the closed pores based on the cumulative pore volume distribution and the differential pore size distribution of the plunger samples and the crushed samples with the different particle sizes, comparing the crushed samples with the optimal crushed particle size with the plunger samples, and calculating closed pore volume opened during crushing the plunger samples into the crushed samples, as shown in FIG. 2(a)-FIG. 2(b), in which FIG. 2(a) is a schematic diagram of the pore volume distribution obtained by the low-field NMR experiments and FIG. 2(b) is a schematic diagram of pore size ranges of the closed pores obtained by the low-field NMR experiments, including:

obtaining a main pore size range of the closed pores according to the cumulative pore volume distribution and the differential pore size distribution of the plunger samples and the crushed samples with the different particle sizes, determining the optimal crushed particle size for opening the closed pores (if the crushed particle sizes are too small, primary interconnected pores in the coal seams and the shales are destroyed, resulting in larger pore volume), comparing the crushed samples with the optimal crushed particle size with the plunger samples, and calculating the closed pore volume $V_{F1}$ opened during crushing the plunger samples into the crushed samples, $$V_{F1} = V_{optimal\ crushed\ samples} - V_{plunger\ samples} \quad (4),$$

where $V_{optimal\ crushed\ samples}$ is pore volume of the crushed samples with the optimal crushed particle size in the low-field NMR freeze-thaw experiments, and $V_{plunger\ samples}$ is pore volume of the plunger samples in the low-field NMR experiments; and S4, carrying out the SAXS experiments on the crushed samples with the optimal crushed particle size of the coal seams and the shales respectively to obtain pore size distribution and pore volume of the total pores in a pore size range of 1-100 nm, including:

S41, carrying out the SAXS experiments on the crushed samples with the optimal crushed particle size, where the SAXS experiments may measure all interconnected pores and the closed pores in the pore size range of 1-100 nm, where the pore size range characterized by the SAXS experiments corresponds to the pore size ranges of the closed pores obtained by the low-field NMR experiments crushing the plunger samples step by step, which may reveal development characteristics of the closed pores in the crushed samples, then converting two-dimensional scattering images into scattering data (relative scattering intensity) by a FIT2D software, and converting relative scattering intensity data of water, glassy carbon and other standard samples in the same experimental environment into absolute scattering intensity of the crushed samples with the optimal crushed particle size;

S42, measuring contents of C, H, O, N, S and other major elements in the crushed samples of the coal seams and the shales by an X-ray fluorescence spectrometer, measuring density data of the standard samples of the coal seams and the shales, and calculating total porosities, pore volume and pore specific surface area of the crushed samples according to a formula (5)–a formula (7);

in the SAXS experiments, the obtained porosities are calculated by a following formula:

$$\frac{1}{r_e^2}\int_0^\infty q^2 \left(\frac{\partial \Sigma}{\partial \Omega}\right)_s (q) dq = 2\pi^2 (\Delta \rho_e)^2 P(1-P), \quad (5)$$

where $\rho$ is the porosities;

$\left(\frac{\partial \Sigma}{\partial \Omega}\right)_s (q)$ is the absolute scattering intensity corrected by the standard samples; $r_e = 2.8179 \times 10^{-13}$ is Thomson electron radius, centimeter (cm); $\Delta \rho_e$ is electron density difference, $eA^{-3}$;

electron density $\rho_e$ is obtained by a following formula:

$$\rho_e = \frac{\rho N_A \Sigma \alpha_i Z_i}{\Sigma \alpha_i M_i}, \quad (6)$$

where $\rho$ is true electron density; $N_A$ is an Avogadro constant; $\alpha$ is a specific element content, i; $Z_i$ is atomic number of elements; $M_i$ is atomic mass;

pore specific surface area of porous materials is calculated by a following formula:

$$S_V = \frac{\pi P(1-P) \lim [q^4 I(q)]}{\int_0^\infty q^2 I(q) dq}, \quad (7)$$

where $S_v$ is the pore specific surface area;

pore size distribution curves of the crushed samples are calculated by importing the scattering data using a McSAS software based on Monte Carlo regression principle and adjusting parameters;

S43, importing the scattering data by using the McSAS software based on the Monte Carlo regression principle, setting corresponding parameters, and obtaining the pore size distribution of the total pores in the pore size range of 1-100 nm; as shown in FIG. 3, differential pore size distribution curves of the SAXS experiments are generally higher than pore size distribution curves of the low-field NMR freeze-thaw experiments, and the pore volume also indicates that there are still a considerable number of the closed pores in the crushed samples, but due to differences in organic matter distribution and mineral composition of the coal seams and the shales, a pore size range of the closed pores of the coal seams and a pore size range of the closed pores of the shales are different, but are also concentrated in a pore size range of micropores and mesopores; and S44, calculating closed pore volume $V_{F2}$ in the pore size range of 1-100 nm:

$$V_{F2} = V_{SAXS} - V_{optimal\ crushed\ samples\ in\ a\ specific\ pore\ size\ range} \quad (8),$$

where $V_{SAXS}$ is the pore volume of the total pores obtained by the SAXS experiments, and $V_{optimal\ crushed\ samples\ in\ the\ specific\ pore\ size\ range}$ is closed pore volume of the crushed samples with the optimal crushed particle size obtained by the low-field NMR freeze-thaw experiments, where the pore volume obtained by the SAXS experiments is mainly in the pore size range of 1-100 nm, and $V_{optimal\ crushed\ samples\ in\ the\ specific\ pore\ size\ range}$ is the pore volume of crushed samples obtained by the low-field NMR freeze-thaw experiments in the pore size range measured by the SAXS experiments;

S5, determining the pore volume of the total pores and total closed pore volume in the coal seams and the shales based on results of the low-field NMR experiments on the plunger samples, the low-field NMR freeze-thaw experiments on the crushed samples and the SAXS experiments on the crushed samples with the optimal crushed particle size;

$$V_{total} = V_{optimal\ crushed\ samples} + V_{SAXS} - V_{optimal\ crushed\ samples\ in\ the\ specific\ pore\ size\ range} \quad (9),$$

and $$V_{Ftotal} = V_{F1} + V_{F2} \quad (10),$$

where $V_{total}$ is the pore volume of the total pores and $V_{Ftotal}$ is the total closed pore volume; and S6, making the plunger samples of the coal seams, the shales and the tight sandstone with the same diameter but different heights according to actual drilling reservoir combinations, as shown in FIG. 4, and carrying out the non-steady overburden permeability experiments on one plunger sample or multiple plunger samples to characterize the connectivity of the coal measure composite reservoirs under influence of pore development and lithologic combinations, including:

S61, dividing the source-reservoir-cap assemblages according to the stratum lithology and the gas and water distribution revealed by drilling cores, determining the vertical distribution of the coal measure composite reservoirs, and obtaining the typical lithologic combination types;

S62, making the plunger samples of the coal seams, the shales and the tight sandstone with the same diameter but the different heights and perpendicular to the bedding direction according to the lithologic combination types; and S63, carrying out the non-steady overburden permeability experiments to quantitatively characterize the connectivity of the coal measure composite reservoirs under influence of stratum pressure conditions and the lithologic combination types, and evaluating the coal measure composite reservoirs combined with the characterization of the closed pores, so as to select favorable coal measure composite reservoirs.

It should be understood that the technical schemes of the present application are not limited to the limits of the above specific embodiments, and any technical variations made according to the technical schemes of the present application, without departing from the scope protected by the

What is claimed is:

1. A characterization method of closed pores and connectivity of coal measure composite reservoirs, comprising:
S1, making coal seams and shales in the coal measure composite reservoirs into plunger samples, and carrying out nuclear magnetic resonance experiments on the plunger samples to obtain porosities, cumulative pore volume distribution and differential pore size distribution of the plunger samples;
S2, crushing the plunger samples of the coal seams and the shales into crushed samples with different particle sizes respectively, and carrying out nuclear magnetic resonance freeze-thaw experiments on the crushed samples to obtain cumulative pore volume distribution and differential pore size distribution of the different particle sizes;
S3, determining an optimal crushed particle size for opening the closed pores in the coal seams and the shales based on the cumulative pore volume distribution and the differential pore size distribution of the plunger samples and the different particle sizes, comparing with the plunger samples, calculating closed pore volume opened in a process of the crushing the plunger samples into the crushed samples;
S4, carrying out small-angle X-ray scattering experiments on crushed samples with the optimal crushed particle size of the coal seams and the shales respectively to obtain pore size distribution and pore volume of total pores in pore size ranges;
S5, determining pore volume of the total pores and closed pore volume in the coal seams and the shales based on experimental results of the nuclear magnetic resonance experiments of the plunger samples, the nuclear magnetic resonance freeze-thaw experiments as well as the small-angle X-ray scattering experiments of the crushed samples;

$$V_{total} = V_{optimal\ crushed\ samples} + V_{SAXS} - V_{optimal\ crushed\ samples\ in\ a\ specific\ pore\ size\ range},$$
and $$V_{Ftotal} = V_{F1} + V_{F2},$$

wherein $V_{total}$ is the pore volume of the total pores, $V_{Ftotal}$ is total closed pore volume, and $V_{F1}$ is the closed pore volume opened in the process of the crushing the plunger samples into the crushed samples;

$$V_{F1} = V_{optimal\ crushed\ samples} - V_{plunger\ samples},$$

wherein $V_{optimal\ crushed\ samples}$ is pore volume of the samples with the optimal crushed particle size in the nuclear magnetic resonance freeze-thaw experiments, and $V_{plunger\ samples}$ is pore volume of the plunger samples by nuclear magnetic resonance; and
S6, making plunger samples of the coal seams, the shales and tight sandstone with a same diameter but different heights according to actual drilling reservoir combinations, and carrying out non-steady overburden permeability experiments by a pressure drop method to quantitatively characterize the connectivity of the coal measure composite reservoirs under influence of stratum pressure conditions and lithologic combinations;
wherein the S4 comprises:
S41, carrying out the small-angle X-ray scattering experiments on the crushed samples with the optimal crushed particle size of the coal seams and the shales to obtain two-dimensional scattering images, then converting the two-dimensional scattering images into scattering data by a FIT2D software, and converting relative scattering intensity data of standard samples in same experimental environment into absolute scattering intensity of the crushed samples with the optimal crushed particle size;
S42, measuring contents of major elements in the crushed samples with the optimal crushed particle size by an X-ray fluorescence spectrometer, measuring density data of the standard samples in the same experimental environment, and calculating total porosities, pore volume and pore specific surface area of the crushed samples with the optimal crushed particle size; and
S43, importing the scattering data by using a McSAS software based on a Monte Carlo regression principle, setting corresponding parameters, and obtaining the pore size distribution and the pore volume of the total pores in a pore size range of 1-100 nm,
wherein a calculation formula of closed pore volume $V_{F2}$ in the pore size range of 1-100 nm is:

$$V_{F2} = V_{SAXS} - V_{optimal\ crushed\ samples\ in\ the\ specific\ pore\ size\ range},$$

wherein $V_{SAXS}$ is the pore volume of the total pores obtained by the small-angle X-ray scattering, and $V_{optimal\ crushed\ samples\ in\ the\ specific\ pore\ size\ range}$ is closed pore volume of the samples with the optimal crushed particle size obtained by the nuclear magnetic resonance freeze-thaw experiments in the pore size range of 1-100 nm;
wherein the S6 comprises:
S61, dividing source-reservoir-cap assemblages according to stratum lithology and gas and water distribution revealed by drilling cores, determining vertical distribution of coal measure reservoirs, and summarizing several typical lithologic combination types;
S62, making the plunger samples of the coal seams, the shales and the tight sandstone with the same diameter but the different heights and perpendicular to a bedding direction according to the lithologic combination types; and
S63, carrying out the non-steady overburden permeability experiments by the pressure drop method to quantitatively characterize the connectivity of the coal measure composite reservoirs under the influence of the stratum pressure conditions and lithologic combinations, and carrying out reservoir evaluation combined with characterization of the closed pores to select favorable coal measure composite reservoirs.

2. The characterization method of the closed pores and the connectivity of the coal measure composite reservoirs according to claim 1, wherein the S1 comprises:
S11, dividing the coal measure composite reservoirs according to the source-reservoir-cap assemblages by a water vapor distribution relationship in a gas-bearing system of coal measures to obtain the coal seams, the shales and the tight sandstone;
S12, collecting fresh borehole samples from the coal seams and the shales to make multiple groups of the plunger samples; and
S13, carrying out the nuclear magnetic resonance experiments on the plunger samples, then measuring transverse relaxation time, and calculating the porosities, the cumulative pore volume distribution and the differential pore size distribution of the plunger samples.

3. The characterization method of the closed pores and the connectivity of the coal measure composite reservoirs according to claim 2, wherein in the S13, the plunger samples used in the nuclear magnetic resonance experiments are vacuumized, pressurized to 15 MPa and saturated with saline for 48 h before measuring the transverse relaxation time.

4. The characterization method of the closed pores and the connectivity of the coal measure composite reservoirs according to claim 1, wherein the S2 comprises:

drying the plunger samples after the nuclear magnetic resonance experiments for 24 h, crushing by a crusher, then sieving into the crushed samples with the different particle sizes by a standard mesh screen, carrying out the nuclear magnetic resonance freeze-thaw experiments on the crushed samples with the different particle sizes, and calculating the cumulative pore volume distribution and the differential pore size distribution of the different particle sizes based on a simplified Gibbs-Thomson thermodynamic equation.

5. The characterization method of the closed pores and the connectivity of the coal measure composite reservoirs according to claim 4, wherein in the nuclear magnetic resonance freeze-thaw experiments, distilled water is used as a probe solution, temperature gradually increases from −33° C. to 0° C., and a temperature duration at each temperature point is 5 min.

\* \* \* \* \*